US00PP27965P2

(12) United States Plant Patent
Hartman

(10) Patent No.: US PP27,965 P2
(45) Date of Patent: May 2, 2017

(54) ***CALADIUM* PLANT NAMED 'WATER'S EDGE'**

(50) Latin Name: *Caladium×hortulanum*
Varietal Denomination: Water's Edge

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 14/998,541

(22) Filed: Jan. 16, 2016

(51) Int. Cl.
*A01H 5/02* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'Water's Edge', characterized by its intermediate height, upright and uniformly mounded plant habit; vigorous growth habit and moderately rapid growth rate; fancy-type leaves with bright white-colored venation, grey green-colored interveinal areas surrounded by dark green borders; relatively high yield of largest grade tubers; and above average tolerance to *Xanthomonas* Leaf Spot.

4 Drawing Sheets

Botanical designation: *Caladium×hortulanum.*
Cultivar denomination: 'WATER'S EDGE'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Water's Edge'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2009 in Avon Park, Fla. of *Caladium×hortulanum* 'Aaron', not patented, as the female, or seed, parent with *Caladium×hortulanum* 'Candidum Senior', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2010.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2011 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Water's Edge'. These characteristics in combination distinguish 'Water's Edge' as a new and distinct *Caladium* plant:

1. Intermediate in height, upright and uniformly mounded plant habit.
2. Vigorous growth habit and moderately rapid growth rate.
3. Fancy-type leaves with bright white-colored venation, grey green-colored interveinal areas surrounded by dark green borders.
4. Relatively high yield of largest grade tubers.
5. Above average tolerance to Xanthomonas Leaf Spot.

Plants of the new *Caladium* differ primarily from plants of the female parent, 'Aaron', in the following characteristics:

1. Plants of the new *Caladium* have a more attractive growth habit than plants of 'Aaron'.
2. Plants of the new *Caladium* and 'Aaron' differ in leaf color as leaves of 'Aaron' have white-colored venation and radiating interveinal areas surrounded with green-colored borders.
3. Plants of the new *Caladium* and 'Aaron' differ in tolerance to *Xanthomonas* Leaf Spot as plants of 'Aaron' are more susceptible to damage resulting from *Xanthomonas* Leaf Spot than plants of the new *Caladium.*
4. Plants of the new *Caladium* produce more tubers of the largest grade sizes than plants of 'Aaron'.

Plants of the new *Caladium* differ primarily from plants of the male parent, 'Candidum Senior', in the following characteristics:

1. Leaves of plants of the new *Caladium* are smaller and flatter than leaves of 'Candidum Senior'.
2. Plants of the new *Caladium* and 'Candidum Senior' differ in leaf color as leaves of 'Candidum Senior' are greenish white in color with medium green-colored venation and thin green-colored margins.

3. Plants of the new *Caladium* and 'Candidum Senior' differ in leaf petiole color as leaf petioles of 'Candidum Senior' are tan green in color with darker-colored stripes, streaks and stippling.
4. Plants of the new *Caladium* produce more tubers of the largest grade sizes than plants of 'Candidum Senior'.

Plants of the new *Caladium* can be compared to plants of *Caladium×hortulanum* 'Candidum', not patented. In side-by-side comparisons, plants of the new *Caladium* differ primarily from plants of 'Candidum' in the following characteristics:

1. Plants of the new *Caladium* and 'Candidum' differ in leaf color as leaves of 'Candidum' have distinct green-colored venation with white-colored interveinal areas.
2. Plants of the new *Caladium* and 'Candidum' differ in leaf petiole color as leaf petioles of 'Candidum' are black in color with green-colored stripes.
3. Plants of the new *Caladium* and 'Candidum' differ in tolerance to *Xanthomonas* Leaf Spot as plants of 'Candidum' are more susceptible to damage resulting from *Xanthomonas* Leaf Spot than plants of the new *Caladium*.
4. Plants of the new *Caladium* produce more tubers of the largest grade sizes than plants of 'Candidum'.

Plants of the new *Caladium* can also be compared to plants of *Caladium×hortulanum* 'Florida Moonlight', disclosed in U.S. Plant Pat. No. 14,565. In side-by-side comparisons, plants of the new *Caladium* differ primarily from plants of 'Florida Moonlight' in the following characteristics:

1. Leaves of plants of the new *Caladium* are smaller and narrower than plants of 'Florida Moonlight'.
2. Plants of the new *Caladium* and 'Florida Moonlight' differ in leaf color as leaves of 'Florida Moonlight' have greenish white-colored leaves and venation.
3. Plants of the new *Caladium* and 'Florida Moonlight' differ in leaf petiole color as leaf petioles of 'Florida Moonlight' are tan pink in color with greenish brown-colored stippling, streaks and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Water's Edge' in a container and grown in a shadehouse (tuber not de-eyed).

The photograph at the top of the second sheet is a comparison view of typical potted plants of the female parent, 'Aaron' (left), 'Water's Edge' (center) and the male parent, 'Candidum Senior' (right).

The photograph at the bottom of the second sheet is a comparison view of typical potted plants of 'Candidum' (left), 'Water's Edge' (center) and 'Florida Moonlight' (right).

The photograph at the top of the third sheet is a comparison view of typical plants of 'Water's Edge' grown in containers; the plant on the left has not had its tuber de-eyed and the plant on the right has had its tuber de-eyed prior to planting.

The photograph at the bottom of the third sheet is a side perspective view of typical plants of 'Water's Edge' grown in an open field.

The photograph at the top of the fourth sheet is a close-up view of a typical freshly-harvested tuber and roots of 'Water's Edge'.

The photograph at the bottom of the fourth sheet is a close-up view of a typical inflorescence of 'Water's Edge'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were ten weeks old and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Water's Edge'.

Parentage:

*Female, or seed, parent.*—*Caladium×hortulanum* 'Aaron', not patented.

*Male, or pollen, parent.*—*Caladium×hortulanum* 'Candidum Senior', not patented.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented and somewhat flattened; individual segments elliptic or irregular in shape. Height: About 5.4 cm. Diameter: About 6.5 cm to 8.8 cm. Segment height: About 3.6 cm. Segment diameter: About 4 cm to 5.5 cm. Axillary buds, height: About 4 mm to 5 mm. Texture: Thick, starchy; somewhat brittle. Color: Epidermis, freshly-harvested: Close to 1788 and 178C. Epidermis, dried: Close to 177A and 200A. Cortical tissue: Close to 159A tinged with close to N170D. Axillary buds: Close to 49C to 49D. Root description: Thick, fleshy contractile roots; color, close to 155C faintly tinged with close to 181D. Rooting habit: Low branching; medium density.

Plant description:

*Plant type*.—Herbaceous perennial; suitable as a potted plant in containers 15-cm to 25-cm and suitable as a landscape plant in shaded areas.

*Plant and growth habit*.—Intermediate in height, upright and uniformly mounded plant habit; vigorous and dense growth habit; rapid growth rate, potted plants in finished or saleable form in about eight weeks after planting tubers; leaf petioles and leaves arise from one or more growing points on tubers; petioles mostly upright and leaning outwardly with development.

*Plant height, from soil level to top of foliar plane, shadehouse-grown potted plants*.—About 28 cm to 35 cm.

*Plant height, from soil level to top of inflorescences, shadehouse-grown potted plants*.—About 34 cm.

*Plant diameter or spread, shadehouse-grown potted plants*.—About 42 cm to 50 cm.

*Number of shoots per plant, shadehouse-grown potted plants, tubers not de-eyed*.—About two to three develop per #1 tuber.

*Number of shoots per plant, shadehouse-grown potted plants, tubers de-eyed*.—About three to four develop per #1 tuber.

*Cataphylls, shadehouse-grown potted plants*.—Length: About 5 cm to 8.5 cm. Width: About 1.5 cm to 1.8 cm. Shape: Lanceolate. Apex: Acute. Base: Sheathing the stem. Color, inner surface: Close to 155D; colors and patterns on the outer surface are visible on the inner surface. Color, outer surface: Close to 159D and 146D, streaked, stippled and mottled with close to 200A tinged with close to 147A; with development, color becoming closer to 200B to 200C.

Leaf description:

*Arrangement and type*.—Alternate; simple; fancy-type.

*Length, shadehouse-grown potted plants*.—About 19.5 cm to 27.2 cm.

*Width, shadehouse-grown potted plants*.—About 12 cm to 18 cm.

*Shape*.—Ovate.

*Apex*.—Acute to acuminate.

*Base*.—Sagittate to peltate.

*Margin*.—Entire; mostly flat with broad undulations.

*Texture, upper and lower surfaces*.—Smooth, glabrous.

*Luster, upper surface*.—Dull sheen.

*Luster, lower surface*.—Glaucous, dull sheen.

*Venation pattern*.—Pinnate.

*Color, shadehouse-grown potted plants*.—Developing and fully expanded leaves, upper surface: Ground color: Close to 147A tinged with close to 137B. Margins: Close to 147B; at the apex, close to 187B. Basal notch: Close to 187A to 187B. Midvein: Close to 192D and close to 155C with close to 195D. Primary veins: Close to 194C mottled and streaked with close to 147B. Areas surrounding venation: Close to 155D. Interveinal areas: Close to 194D and a suffusion of close to 137A, 137B, 194C to 194D and 194D. Developing and fully expanded leaves, lower surface: Ground color: Close to 191A. Margins: Close to 147B; at the apex, close to 187B. Basal notch: Close to 187A to 187B. Midvein: Close to 194C and close to 194C to 194D. Primary veins: Close to 193A to 193B and close to 147C. Secondary veins: Close to 147A to 147B. Areas surrounding venation: More white than close to 155C. Interveinal areas: Close to a suffusion of close to 147D and 145D.

*Petioles*.—Aspect: Initially upright and straight; with development, leaning outwardly; flexible. Length, shadehouse-grown potted plants: About 24 cm to 28.5 cm. Diameter, distally, shadehouse-grown potted plants: About 5 mm to 6 mm. Diameter, proximally, shadehouse-grown potted plants: About 1 cm to 1.2 cm. Texture: Smooth, glabrous; glaucous. Color, shadehouse-grown potted plants: Close to 147B and close to 147B tinged with close to 137B, variably and sparsely stippled, streaked and tessellated with close to 147A to 147B; or close to 147B sparsely stippled, streaked and tessellated with close to 200C; below the leaf and petiole junction, close to 147D. Wing length, shadehouse-grown potted plants: About 3.5 cm to 5.5 cm. Wing diameter, shadehouse-grown potted plants: About 1 cm. Texture, inner and outer surfaces: Smooth, glabrous. Luster, inner and outer surfaces: Dull. Wing color, shadehouse-grown potted plants: Inner surface: Close to 155D tinged with close to 145D; colors and patterns on the outer surface are visible on the inner surface. Outer surface: Close to 159D and 146D streaked, stippled and mottled with close to 200B to 200C tinged with close to 147A.

Inflorescence description: Inflorescences observed on ten week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with mint-like camphor note.

*Natural flowering season and flower longevity*.—Plants of the new *Caladium* typically flower during the spring and summer in central Florida; flowers develop about ten weeks after growth commences; inflorescences last about three days before fading; inflorescences persistent.

*Spathe*.—Length, overall: About 11.8 cm. Length, distal open portion: About 7.1 cm. Length, proximal closed portion: About 4.7 cm. Width, distal open portion: About 3.7 cm. Depth, distal open portion: About 2.7 cm. Width, at constriction: About 1.2 cm. Width, proximal closed portion: About 2.4 cm. Shape: Elliptic. Apex: Acuminate. Base: Obtuse. Margin: Entire. Texture, front and rear surfaces: Smooth, glabrous. Luster, front surface: Dull sheen. Luster, rear surface: Glaucous, dull sheen. Color, front surface: Distal open portion: Close to 155C; margins variably tinged with close to 193C; with development, color becoming closer to 200C and 200D. Proximal closed portion: Close to 147C; color does not change with development. Color, rear surface: Distal open portion: Whiter than 155C, variable areas, close to 147D tinged with close to 146D; color does not change with development. Proximal closed portion: Close to 147A and 147B mottled with close to 147C and 147D; color does not change with development.

*Spadix*.—Length, overall: About 7.1 cm. Length, male flower zone: About 4.6 cm. Length, sterile zone: About 1.5 cm. Length, female flower zone: About 1 cm. Diameter, male flower zone: About 1 cm. Diameter, sterile flower zone: About 7 mm. Diameter, female flower zone: About 1 cm. Shape: Columnar, spindle-shaped. Apex: Acute to obtuse. Base: Obtuse. Aspect: Upright. Color, mature, male zone: Close to 158D tinged with close to 4D. Color, mature, sterile zone: Close to 158D. Color, mature, female zone: Close to 155C and 36D. Male flowers: Quantity per spadix: About 165. Shape: Obovate. Height: About 3 mm. Diameter: About 3 mm. Pollen amount: Moderate. Pollen color: Close to 4C. Female flowers: Quantity per spadix: About 48. Shape: Obovate. Height: About 2.5 mm. Diameter: About 2.5 mm. Stigma color: Close to 155C. Ovary color: Close to 36D.

*Scape*.—Length: About 22.2 cm. Diameter: About 8.5 mm. Strength: Sturdy; rigid and somewhat flexible. Aspect: Mostly erect. Texture: Smooth, glabrous. Luster: Slightly glossy; below spathe, glaucous. Color: Close to 147B to 147C tinged with close to 145B; just below spathe, close to 147C to 147D.

*Seeds and fruits*.—To date, seed and fruit development have not been observed on plants of the new *Caladium*.

Disease & pest tolerance: Plants of the new *Caladium* have been observed to have above average tolerance to *Xanthomonas* Leaf Spot. Plants of the new *Caladium* have been observed to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'Water's Edge' as illustrated and described.

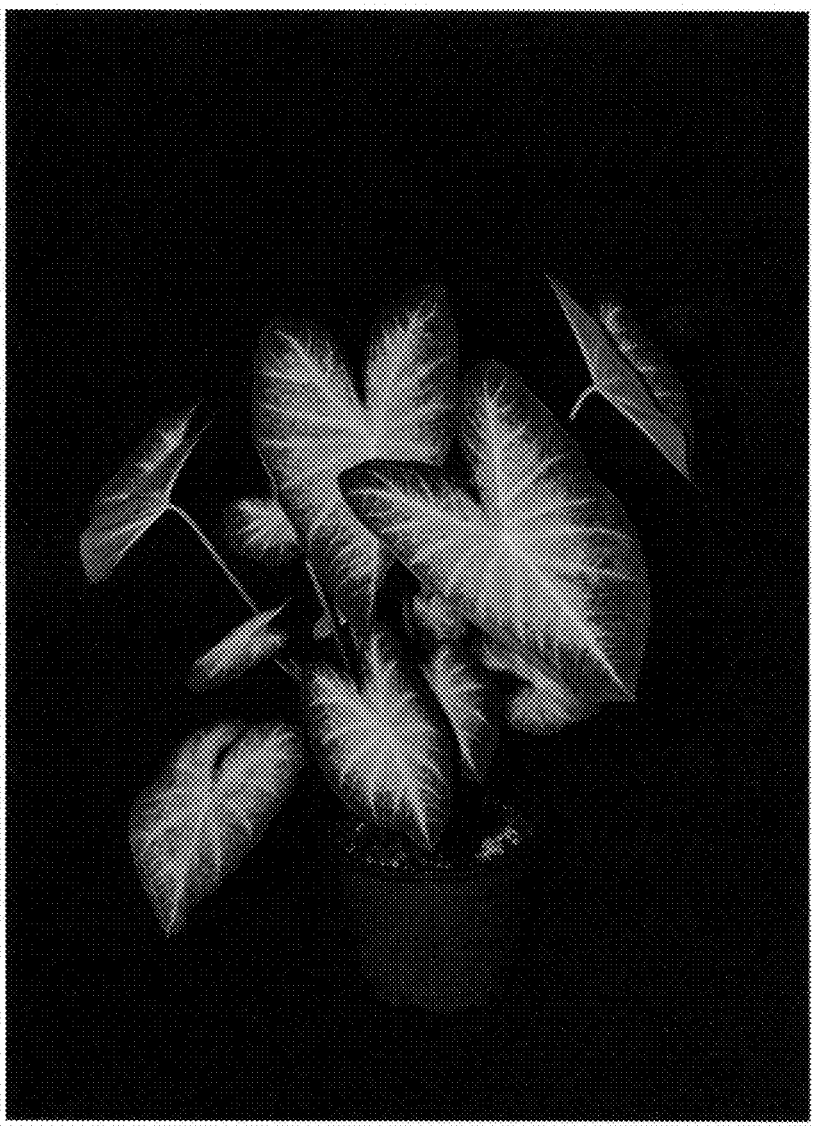

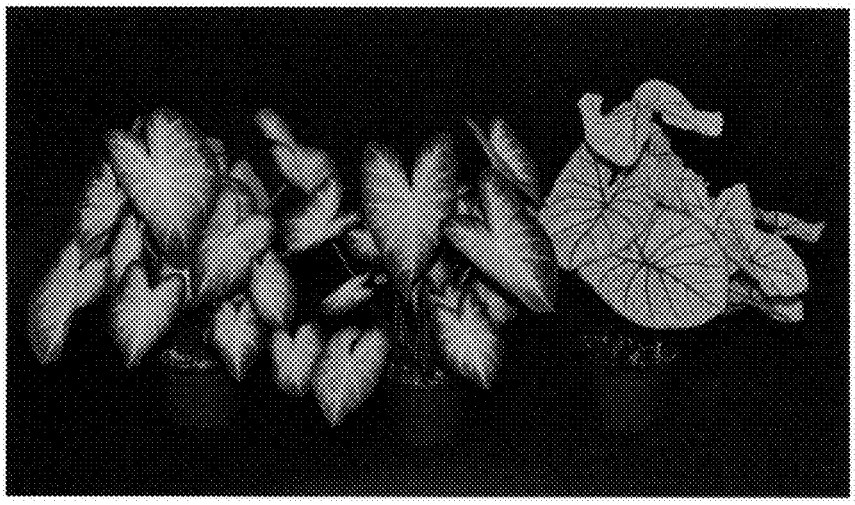
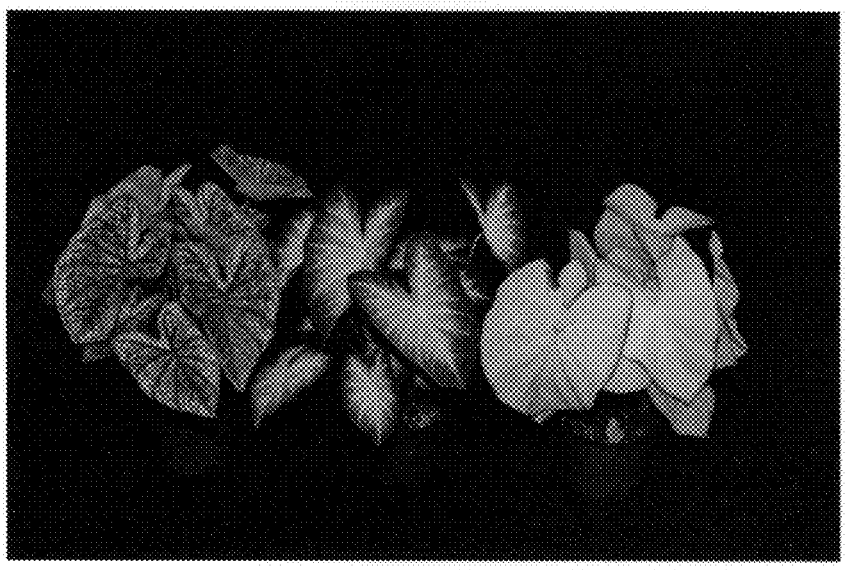

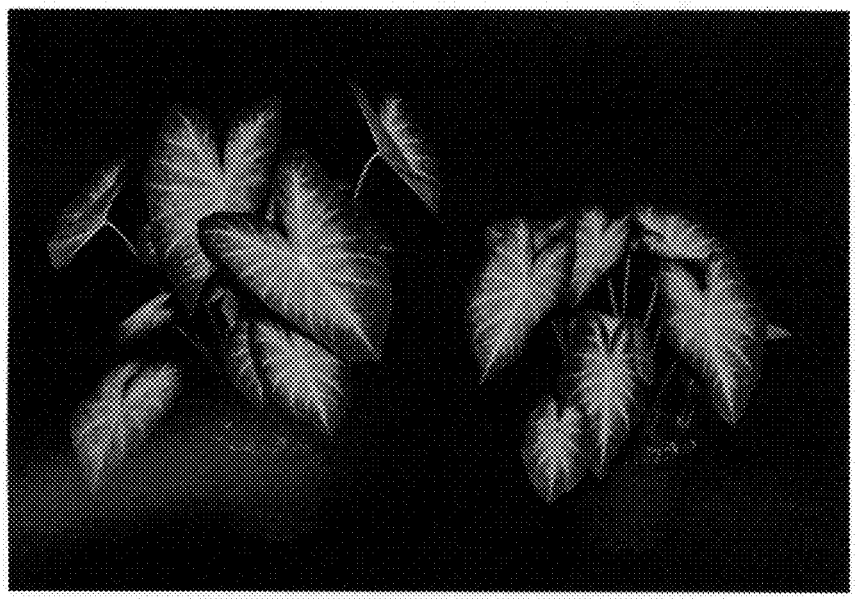
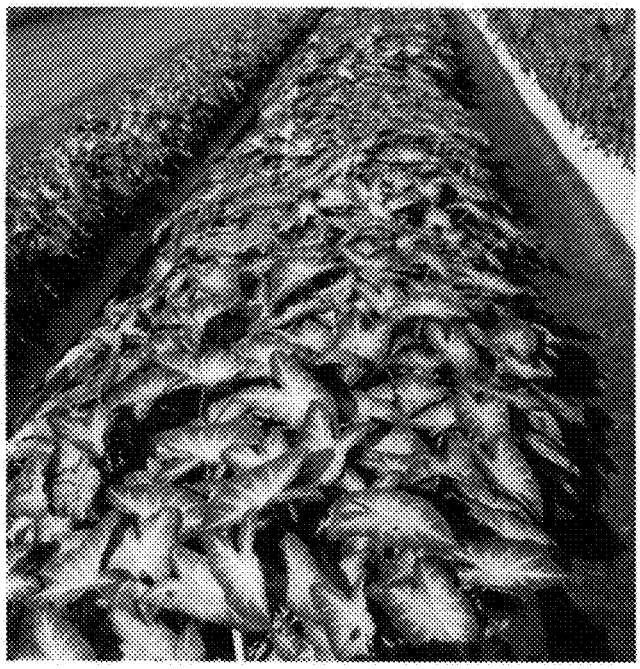

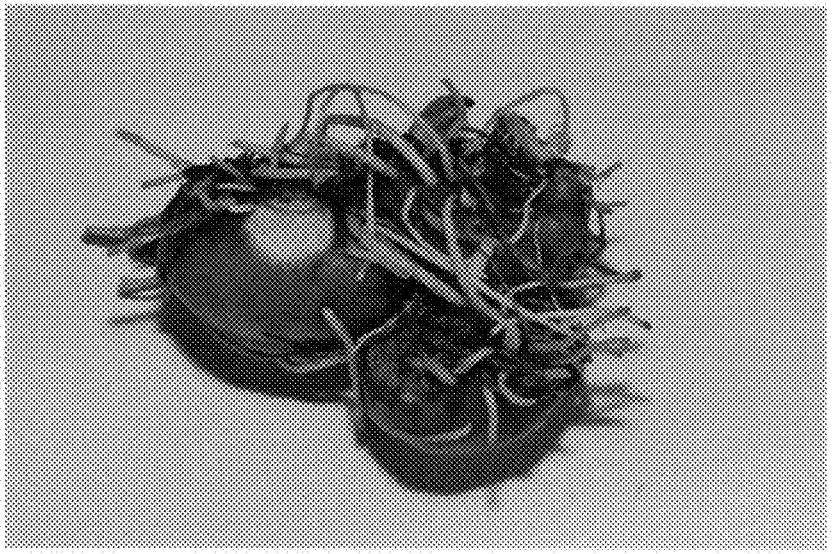
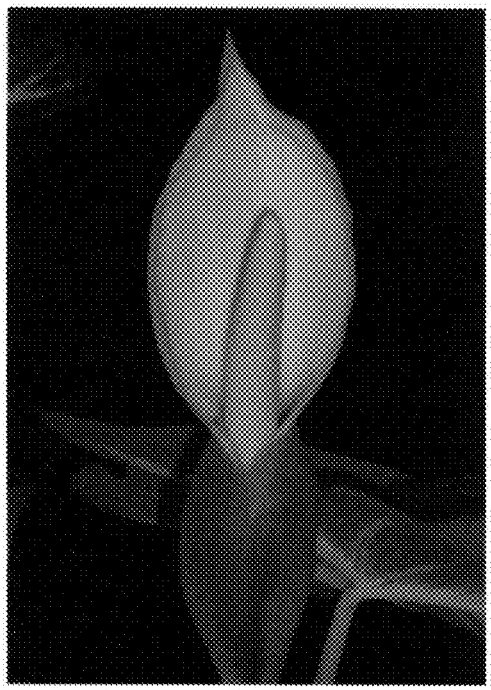

* * * * *